United States Patent [19]

Prencipe et al.

[11] Patent Number: 5,300,283
[45] Date of Patent: Apr. 5, 1994

[54] VISCOELASTIC DENTIFRICE COMPOSITION

[75] Inventors: Michael Prencipe, East Windsor; Gary A. Durga, Edison, both of N.J.

[73] Assignee: Colgate Palmolive Company, Piscataway, N.J.

[21] Appl. No.: 51,319

[22] Filed: Oct. 22, 1992

Related U.S. Application Data

[62] Division of Ser. No. 738,766, Aug. 1, 1991, Pat. No. 5,202,112.

[51] Int. Cl.$^5$ .......................... A61K 7/16; A61K 7/18
[52] U.S. Cl. .................................. 424/49; 424/52
[58] Field of Search ....................... 424/49-58

[56] References Cited

U.S. PATENT DOCUMENTS

| | | | |
|---|---|---|---|
| 3,963,832 | 6/1976 | Hashimoto et al. | 424/56 |
| 4,208,009 | 5/1980 | Gaffar et al. | 424/49 |
| 5,032,386 | 7/1991 | Gaffar et al. | 424/49 |
| 5,034,488 | 7/1991 | Tazi et al. | 526/271 |
| 5,064,553 | 11/1991 | Dixit et al. | 252/94 |
| 5,180,578 | 1/1993 | Gaffar et al. | 424/52 |
| 5,188,821 | 2/1993 | Gaffar et al. | 424/52 |
| 5,192,530 | 3/1993 | Gaffar et al. | 424/52 |
| 5,192,531 | 3/1993 | Gaffar et al. | 424/52 |
| 5,202,112 | 4/1993 | Prencipe et al. | 426/52 |
| 5,232,621 | 8/1993 | Dixit et al. | 252/174.23 |

*Primary Examiner*—Shep K. Rose
*Attorney, Agent, or Firm*—Robert L. Stone; Murray M. Grill; Robert C. Sullivan

[57] ABSTRACT

A toothpaste or dental gel composition containing an amount of a synthetic linearly viscoelastic cross-linked polymeric thickening agent, especially a cross-linked methyl vinyl ether/maleic anhydride copolymer, effective to render the composition linearly viscoelastic, and a method of promoting oral hygiene by applying an effective amount of the composition to dental surface.

14 Claims, No Drawings

VISCOELASTIC DENTIFRICE COMPOSITION

This is a division of application Ser. No. 07/738,766 filed Aug. 1, 1991 now U.S. Pat. No. 5,202,112.

This invention relates to novel dentifrice compositions, especially to toothpastes and dental gels having viscoelastic properties.

A thickening agent (binding or gelling agent) is commonly employed in dentifrice compositions to prevent separation of ingredients in storage, promote dispensability and retention in use as on a toothbrush, improve cosmetic properties and the like. Such thickeners are generally hydrophilic colloids which disperse in aqueous media. The most widely used thickeners are cellulose derivatives because they are cheap and their quality can be closely controlled. Sodium carboxymethyl cellulose (NaCMC) is the most widely used thickener in dentifrices but such thickened dentifrices are often subject to syneresis, i.e. severe loss of rigidity and viscosity. It is believed that this may be caused partly by enzymatic degradation of the NaCMC by cellulytic enzyme (cellulase) which can be produced by moulds and bacteria present in some batches of NaCMC. These microorganisms may originate in the water, or on storage of the NaCMC, in damp conditions which support growth, or from other sources of contamination. Killing the organism responsible does not, of course, remove the enzyme already produced.

Hydroxyethyl cellulose is a thickener with a better resistance to cellulytic attack than NaCMC, possibly due to its more uniform substitution pattern along the molecule compared with NaCMC, but in dentifrice formulations, it often produces a product with an unacceptably "long" or "stringy" texture.

U.S. Pat. No. 4,254,101 to Denny proposes the use of carboxyvinyl polymers as thickeners in toothpastes containing silica abrasive polishing materials and high levels of humectant materials to provide "excellent texture" and improved fluoride ion availability to dental enamel. The carboxyvinyl polymers are disclosed as colloidally water soluble polymers of acrylic acid cross-linked with about 0.75% to 2.0% of polyallyl sucrose or polyallylpentaethrythritol, obtainable under the Carbopol trademark from B. F. Goodrich. It is known, however, that Carbopol is hard to disperse. B. F. Goodrich suggests the use of an eductor and other specialized procedures to get good dispersions. The problem arises because Carbopol is so hydrophilic that the individual particles swell and the particles clump to form aggregates. When dispersion is attempted, the outside of the aggregate hydrates and swells. The inside is no longer readily contacted with water. This causes fish eyes and regions of inhomogeneity that are very hard to remove by further mixing. The fish eyes and inhomogeous dispersion persist in the final product. The result is decreased control over the final rheological properties of the product and increased batch to batch variation. These variations are readily perceived by the end user and are interpreted as poor quality product.

It is an object of this invention to provide dentifrice compositions which will not be subject to the aforementioned deficiencies. Another object of this invention is the provision of a linear viscoelastic dentifrice composition. Still another object of this invention is the provision of a linear viscoelastic dentifrice composition having excellent stability against phase separation or syneresis, viscosity change in storage, and settling of dissolved, dispersed or suspended particles under high and low temperature conditions, freedom from fish eyes, excellent texture and other cosmetic properties, ease of extrusion from a dispensing tube, pump or the like (easily shear thinned), good stand-up after extrusion (quick recovery of structure), and improved fluoride ion availability to dental enamel leading to improved anti-caries effects. A further object of this invention is the provision of a method for promoting oral hygiene by applying to dental surface, including teeth, preferably in the oral cavity an effective amount of the compositions of this invention. Other objects and advantages will appear as the description proceeds.

In accordance with certain of its aspects the attainment of the objects of this invention is realized by the provision of a linear viscoelastic dentifrice composition in the form of a toothpaste or dental gel with a pH of about 4 to about 9 comprising an orally acceptable water/humectant vehicle, an orally acceptable dental polishing agent and, in an amount effective to render the composition linearly viscoelastic, a synthetic linearly viscoelastic cross-linked polymeric thickening agent having in a 1 wt. % aqueous solution an elastic or storage modulus $G'$ and a viscous or loss modulus $G''$ substantially independent of frequency in an applied frequency range of 0.1 to 100 radians/sec, a $G'$ minimum value of 1,000 dynes/sq.cm which varies less than 1 order of magnitude of its original value, and a ratio of $G''/G'$ ranging from more than 0.05 to less than 1.

The linear viscoelastic aqueous dentifrice compositions of this invention will, at least in the preferred embodiments, satisfy each of the following stability criteria over the aging temperature-time schedule shown by the following Table A:

TABLE A

| Aging Temperature (°F.) | Minimum Duration (Weeks) |
|---|---|
| 120 | 9 |
| 100 | >12 |
| 77 | >52 |

More specifically, the compositions are considered stable if each of the following stability criteria is satisfied for at least the minimum number of weeks for each aging temperature shown in Table I:

a. no significant visible phase separation (i.e. no solid/liquid separation)

b. no significant change in viscosities, yield stress or other dynamic-mechanical properties, c. no discolorization or significant color change.

As used herein, "linear viscoelastic" means that the elastic (storage) modulus ($G'$) and the viscous (loss) modulus ($G''$) of the dentifrice are both substantially independent of strain in an applied strain range of from 0.1%–10%. Dynamic oscillatory measurements are performed using the Rheometrics System Four instrument. In this experiment an oscillatory shear field is imposed on the material, and the corresponding shear stress response is measured. The stress is defined by a component in phase with the displacement (elastic modulus, $G'$) and a component 90° out of phase (loss modulus, $G''$). The value of $G'$ indicates the degree of elasticity and network formation in the system; see 1. Menjivar, J. A., "Water Soluble Polymers; Beauty with Performance"; Glass, J. E., Ed; Advances in Chemistry 213; American Chemical Society, Washington, D.C. 1986, pp 209-226; and 2. Sinton, S.; Maerker, J.; J. Rheol. (N.Y.) 1986 30, 77, both incorporated herein by reference.

More specifically, a dentifrice composition is considered to be linear viscoelastic for purposes of this invention, if over the strain range of 0.1% -50% the elastic modulus G' has a minimum value of 1000 dynes/sq.cm., and varies less then about 1 order of magnitude of its original value. Preferably, the minimum value of G' and maximum variation of G' applies over the strain range of 0.1% to 50%.

As a further characteristic of the preferred linear viscoelastic dentifrice compositions the ratio of G''/G' (Tan δ) is less than 1, preferably less than 0.8, but more than 0.05, preferably more than 0.2, at least over the strain range of 0.1% to 50%. It should be noted in this regard that % strain is shear strain×100%.

With respect to 1 wt. % aqueous solutions of the required cross-linked polymer, elastic moduli G' substantially independent of frequency and higher than the corresponding loss moduli G'' indicate solid-like behavior characteristic of gel structure: see 3. Prud'homme, R. K.; Constien, V., and Knoll, S.; "Polymers in Aqueous Media"; Glass, J. E., Ed; Advances In Chemistry 223; American Chemical Society, Washington, D. C., 1989, pp. 89-112, also incorporated herein by reference.

In such solutions, more specifically, G' and G'' are substantially independent of frequency in an applied frequency range of 0.1 to 100 radians/sec, G' has a minimum value of 1,000 dynes/sq.cm. which varies less than 1 order of magnitude of its original value, and the ratio G''/G' ranges from more than 0.05 to less than 1.

By way of further explanation, the elastic (storage) modulus G' is a measure of the energy stored and retrieved when a strain is applied to the composition, while viscous (loss) modulus G'' is a measure of the amount of energy dissipated as heat when strain is applied. Therefore, a value of Tan δ corresponding to:

$$0.05 < \text{Tan } \delta < 1,$$

preferably
$$0.2 < \text{Tan } \delta < 0.8$$

means that the compositions will retain sufficient energy when a stress or strain is applied, at least over the extent expected to be encountered for products of this type, for example, when squeezed out of a toothpaste tube or pump to return to its previous condition and exhibit excellent stand-up when the stress or strain is removed. The compositions with Tanδ values in these ranges, therefore, will also have a high cohesive property, namely, when a shear or strain is applied to a portion of the compositions to cause it to flow, the surrounding portions will follow. As a result of this cohesiveness of the linear viscoelastic characteristic, the compositions will readily flow uniformly and homogeneously from a pump or tube when it is squeezed thereby contributing to the stand-up and ease of extrusion properties which characterize the compositions of this invention. The linear viscoelastic property also contributes to improved physical stability against phase separation of suspended particles by providing a resistance to movement of the particles due to the strain exerted by a particle on the surrounding fluid medium.

From another aspect, a desirable rheological property which the cross-linked polymers employed herein display in solution which indicates gel network formation is the presence of a yield point. Yield point is defined as the amount of shear stresses needed to initiate flow; see 4. Goodwin, J. W., "Solid/Liquid Dispersions"; Tadros, Th. F., Ed; Academic Press, N.Y., 1987, pp 199-224, also incorporated herein by reference. At shear stress values lower than the yield point, no flow occurs. This plastic rheology is desirable because when the gel displays a sufficiently high yield value it allows permanent suspensions of particles that are formulated in the gel. This is especially important in dentifrices, where suspension of abrasive particles is necessary. see 5. Lockhead, R. Y., Davidson, J. A., and Thomas, G.M.; "Polymers in Aqueous Media: Performance Through Association"; Glass, J. E., Ed; Advances in Chemistry 223; American Chemical Society, Washington, D.C., 1989, pp 113-147, also incorporated herein by reference.

The above-described linear viscoelastic properties of the dentifrice compositions of this invention are fundamentally provided by the defined synthetic linearly viscoelastic cross-linked polymeric thickening agents which generally have a molecular weight (M.W.) of about 1,000 to about 5,000,000. The homopolymers and copolymers (from 2, 3 or more monomers) to be cross-linked are generally anionic comprising a chain or backbone containing repeating units each preferably containing at least one carbon atom (typically only carbon atoms in the chain or backbone) and preferably at least one directly or indirectly pendant monovalent acidic group, e.g. sulfonic, phosphinic, or preferably phosphonic or carboxylic, or salt thereof, e.g. alkali metal or ammonium. It is ordinarily desirable that the repeating units constitute at least about 10%, preferably at least about 50%, more preferably at least about 80% up to 95% or 100% by weight of the polymer. Preferably, about 0.02 to about 5%, more preferably about 0.1 to about 2.5% of the cross-linked polymer is employed in the dentifrice compositions herein.

According to a preferred embodiment, the required crosslinked polymer is derived from a synthetic anionic polymeric polycarboxylate, many types of which are disclosed in the prior art, for example, as anticalculus agents in U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al.

These synthetic anionic polymeric polycarboxylates are often per se employed in the form of their free acids or preferably partially or more preferably fully neutralized water soluble or water swellable (hydratable, gel/-forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride (MVE/MA) having a molecular weight (M.W.) of about 30,000 to about 1,000,000. These copolymers are available, for example, as Gantrez e.g. AN 139 (M.W. 500,000), AN 119 (M.W. 250,000); and S-97 Pharmaceutical Grade (M.W. 70,000), of GAF Corporation. Also useful are terpolymers such as 1.0 MA/0.4 MVE/0.1 dodecane, 1.0 MA/0.75MVE/0.25 decene, 1.0 MA/0.95MVE/0.05 eicosene or tetradecene, 1.0 MA/0.9MVE/0.1 tetradecene, 1 MA/0.9MVE/0.1 acrylic acid, vinylpyrrolidone or isobutane.

Other operative polymeric polycarboxylates include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available, for example, as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrollidone.

Additional operative polymeric polycarboxylates disclosed in above referred to U.S. Pat. Nos. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

The synthetic anionic polymeric polycarboxylate component is most often a hydrocarbon with optional halogen and O-containing substituents and linkages as present in, for example, ester, ether and OH groups.

According to another preferred embodiment of this invention, the required cross-linked polymer is derived from a polymer containing repeating units in which one or more phosphonic acid groups are bonded to one or more carbon atoms in the polymer chain. Examples of such polymers are poly (vinyl phosphonic acid) containing units of the formula:

$$-[CH_2-CH]-, \quad\quad I$$
$$\quad\quad |$$
$$\quad\quad PO_3H_2$$

a copolymer having units of vinyl phosphonic acid of formula I alternating or in random association with units of vinyl phosphonyl fluoride, poly(1-phosphonopropene) with units of the formula:

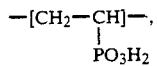
II poly (beta styrene phosphonic acid) containing units of the formula:

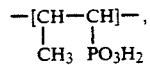
III wherein Ph is phenyl, a copolymer of beta styrene phosphonic acid with vinyl phosphonic acid having the units of formula III alternating or in random association with units of Formula I above and poly (alpha styrene phosphonic acid) containing units of the formula:

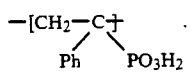
IV

These styrene phosphonic acid polymers and their copolymers with other inert ethylenically unsaturated monomers generally have molecular weights in the range of about 2,000 to about 30,000, preferably about 2,500 to about 10,000. Such "inert" monomers are those which do not significantly interfere with the intended function of the cross-linked polymer.

Other phosphonic-containing polymers include, for example, phosphonated ethylene having units of the formula.

$$-[CH_2)_{14}CHPO_3H_2]_n- \quad\quad V$$

where n may, for example, be an integer or have a value giving the polymer a molecular weight of about 3,000; sodium poly (1,2 butene-4,4-diphosphonate) having units of the formula:

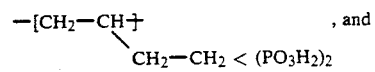
, and VI poly (allyl bis (phosphonoethyl amine) having units of the formula:

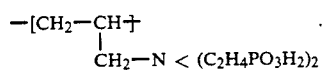
VII

Still other phosphonated polymers include, for example, poly (allyl phosphono acetate), phosphonated polymethacrylate, etc. and the geminal diphosphonate polymers disclosed in EP Publication 0321233.

As illustrative of polymers containing phosphinic acid and/or sulfonic acid groups, there may be mentioned polymers and copolymers containing units or moieties derived from the polymerization of vinyl or allyl phosphinic and/or sulfonic acids. Mixtures of these monomers may be employed, and copolymers thereof with one or more inert polymerizable ethylenically unsaturated monomers such as those described above with respect to the operative synthetic anionic polymeric polycarboxylates. As will be noted, in these and other cross-linkable polymers for use herein, usually only one acidic group is bonded to any given carbon or other atom in the polymer backbone or branch thereon. Polysiloxanes containing or modified to contain pendant acidic groups may also be employed herein. Also effective are ionomers containing or modified to contain acidic groups. Ionomers are described on Pages 546-573 of the Kirk-Othmer Encyclopedia of Chemical Technology, third edition, Supplement volume, John Wiley and Sons, Inc. copyright 1984, which description is incorporated herein by reference. Also effective, provided they contain or are modified to contain acidic groups, are polyesters, polyurethanes and synthetic and natural polyamides including proteins and proteinaceous materials such as collagen, poly (arginine) and other polymerized amino acids.

The cross-linkable polymers and copolymers described above can contain moieties in the chain or backbone derived from polymerizable ethylenically unsaturated monomers in addition to and different from the described acidic group-containing monomeric moieties. Polymerization is conducted in known manner, often in the presence of an initiator, and preferably by slurry polymerization in a solvent medium in which the monomers but not the polymer products are soluble or readily dispersible.

For purposes of this invention, the above-described polymers must be cross-linked to be linearly viscoelastic. The polymers are lightly cross-linked so that they swell and form gels, strong three-dimensional networks in aqueous systems. Excessive cross-linking leading leading to hard, irreversible polymers is to be avoided. The amount of cross-linking agent can vary from about 0.01 to about 30 wt. % of the total, cross-linked polymer, preferably about 2 to about 20 wt. %, more preferably about 3 to about 15 wt. %.

According to a preferred embodiment, cross-linking is carried out concurrently during polymerization of the monomeric components of the polymer by including therein the requisite amount of cross-linking agent. In this embodiment, the cross-linking agents are typically hydrocarbons of at least 4, preferably at least 5, up to about 30, carbon atoms containing 2, less preferably 3 or more, polymerizable activated ethylenically unsaturated groups preferably in non-conjugated, terminal relationship. They can contain optional halogen and/or oxygen-containing substituents and linkages such as ester, ether and OH groups. Examples of such cross-linking agents include 1,7-octadiene, 1,9-decadiene, 1,5-hexadiene, divinyl glycol, butanediol divinyl ether, N,N'-methylenebisacrylamide, polyethylene glycol diacrylates and dimethacrylates which in each case are derived from polyethylene glycol with a molecular weight of 126 to 8500, trimethylolpropane triacrylate and trimethacrylate, ethylene glycol, propylene glycol, butanediol, hexanediol and dodecanediol diacrylates and dimethacrylates, the diacrylates and dimethacrylates of block copolymers derived from ethylene oxide and propylene oxide, multivalent alcohols (e.g. glycerol, sucrose or pentaerythritol) di- or triesterified with acrylic acid or methacrylic acid, triallylamine, tetraallylethylenediamine, divinylbenzene, diallyl phthalate, polyethylene glycol divinyl ether, trimethylolpropane diallyl ether, polyallyl sucrose and pentaerythritol, and divinylethylene urea and mixtures thereof.

According to another embodiment, cross-linking can be achieved after the cross-linkable polymer is formed (postpolymerization) by reaction with amounts of polyfunctional cross-linking agents reactive with corresponding amounts of pendant reactive groups along the polymer chain, e.g. OH, $NH_2$, $CONH_2$ and especially the aforementioned acidic (e.g. carboxylic, phosphonic, phosphinic, sulfonic, etc.) groups in the polymer. Cross-linking agents reactive with the acidic groups usually contain at least about 4 up to about 30 carbon atoms and may include, for example, linear and cyclic polyols such as butane and octadecane diols, polyethylene glycol, glycerol, sucrose and pentaerythritol, and the corresponding polythiols and polyamines such as hexamethylene and octadecane diamines and the like. Cross-linking agents reactive with other of the aforesaid pendant reactive groups include the corresponding polyfunctional acidic compounds, e.g. containing at least 2 of the foresaid acidic groups such as butane, decane and octadecane dicarboxylic acids. Post-polymerization is usually less preferred since the resulting cross-linked products often tend to be more easily subject to hydrolysis or the like with resulting loss of the desired linearly viscoelastic properties.

It will be understood that for post-polymerization cross-linking of maleic anhydride-containing polymers and copolymers, the anhydride ring must first be opened by hydrolysis to release the free —COOH groups needed for reaction with the cross-linking agent.

The water/humectant vehicle in the dentifrice compositions of this invention usually comprises about 6 to about 50% of water and about 20 to about 70% of humectant (or mixture thereof) by weight of the dentifrice composition. The humectants content preferably ranges from about 25 to about 60% on a pure basis and the water content preferably ranges from about 15 to about 30%. The humectants/water ratio preferably ranges from about 1/1 to about 4/1.

Non-toxic, orally acceptable humectants suitable for use in these dentifrice compositions include, for example, sorbitol (usually in the form of a 70% aqueous solution), glycerine, propylene glycol, xylitol, polypropylene glycol and/or polyethylene glycol (e.g. 400–600), especially mixtures of glycerine and sorbitol. In clear gels where the refractive index is an important consideration, a mixture of about 0 to about 80% of glycerine and about 20 to about 80% of sorbitol with about 3 to about 30% of water is preferably employed.

The present dentifrice compositions also contain an orally or dentally acceptable abrasive or polishing material for use in conjunction with a brushing of the teeth. Examples of such polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 4,070,510 of Dec. 15, 1962 such as melamine-, phenolic-, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 $cm.^2$/gm., silica gel or colloidal silica, and complex amorphous alkali metal aluminosilicate.

A silica polishing agent is preferred for use herein. Especially preferred are the colloidal silicas such as those sold under the Zeodent trademark, e.g. Zeodent 113, or under the trademark SYLOID as Syloid 72 and Syloid 74 or under the trademark SANTOCEL as Santocel 100 and alkali metal aluminosilicate complexes. These polishing agents are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may and is preferably reduced or eliminated by washing with water if desired. The insoluble alkali metal metaphosphate is typically employed in powder form of a particle size such that no more than about 1% of the material is larger than about 37 microns.

The polishing material is generally present in amounts ranging from about 5 to about 70%, preferably about 10 to about 40%, more preferably about 10 to about 30%.

A desirable optional component of the dentifrice compositions of this invention is an effective amount of fluoride ions which are well known in the art for inhibiting, preventing or eliminating caries. Fluoride-providing sources generally include compounds which may be slightly or fully soluble in water and the dentifrice compositions in the small amounts needed or permitted to be effective. They are characterized by their ability to release fluoride (or fluoride-containing) ions in water and by freedom from undesired reaction with other components of the oral preparation. Among these materials are inorganic fluoride salts, such as soluble alkali metal and alkaline earth metal salts, for example, sodium fluoride, potassium fluoride, ammonium fluoride, calcium fluoride, a copper fluoride such as cuprous fluoride, zinc fluoride, barium flouride, sodium fluorsilicate, ammonium fluorosilicate, sodium fluorozirconate, sodium monofluoro-phosphate, aluminum mono-and difluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a nontoxic amount, generally about 0.005 to about 3.0% in the preparation. In a dentifrice preparation, e.g. gel, cream, toothpaste, an amount of such compound which releases about 25 to about 5,000 ppm of F ion suitable minimum amount of such compound may be used, but is preferable to employ sufficient compound to release about 300 to about 2,000 ppm, more preferably about 800 to about 1,500 ppm of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1-3%, more typically about 0.76%.

It will be understood that other conventional thickeners (binding, gelling agents) may be included in these dentifrice compositions, usually in amounts ranging from about 0.1 to about 4 parts per part by weight of the defined cross-linked polymeric thickener. Examples of such other thickeners include xanthan gum, hydroxyethyl cellulose and water-soluble salts of cellulose ethers such as sodium carboxymethyl cellulose and sodium carboxymethyl hydroxyethyl cellulose. Natural gums such as carrageenan (Irish moss, Viscarin), gum karaya, gum arabic, and gum tragacanth can also be used. Colloidal magnesium aluminum silicate, Veegum or finely divided silica can be used as part of the thickening agent system. Preferred thickening agents include xanthan gum, carrageenan, sodium carboxymethyl cellulose, sodium carboxymethyl hydroxyethyl cellulose and hydroxyethyl cellulose, preferably in proportions of about 0.4 to about 3 parts per part of the cross-linked polymeric thickner. Also useful is synthetic hecterite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickners include starch, polyvinylpyrrolidone, hydroxybutyl methyl cellulose, hydroxypropyl methyl cellulose, alginates, gum ghatti, locust bean gum, pectens, and tamarind gum and the like.

It will be understood that, as is conventional, the oral preparations are to be sold or otherwise distributed in suitable labelled packages. Thus toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increases prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfacants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effort in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention such as whitening agents, preservatives, silicones, chlorophyll compounds, other anticalculus agents, and/or ammoniated material such as urea, diammonium phosphate, and mixtures thereof. The adjuvants, where present, are incorporated in the preparations in amounts which do not significantly adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, majaram, cinnamon, lemon, and orange, and methyl salicylate. Suitable sweetening agents include sucrose, lactose, maltose, sorbitol, xylitol, sodium cyclamate, perillartine, APM (aspartyl phenyl alanine, methyl ester), saccharine and the like. Suitably, flavor and sweetening agents may together comprise from about 0.1% to 5% more of the preparation.

In the preferred practice of this invention, these dentifrice compositions are preferably applied to dental surface, e.g. tooth enamel, preferably by brushing, regularly such as 1 to 3 times daily, followed preferably by rinsing the oral cavity.

The following Examples A–F illustrate the preparation of operative synthetic cross-linked polymers and their properties. All parts, amounts and proportions referred to herein and in the appended claims are by weight, and temperatures are in degrees C unless otherwise indicated.

| Post Polymerization Cross-Linking | | |
|---|---|---|
| | Example A | Example B |
| PVM/MA* | 0.33330 Moles | 0.33001 Moles |
| PEG 600** | 0.00166 Moles | 0.00249 Moles |
| MEK*** | 6.6 | 6.6 |

*Gantrez AN139, vinylmethyl ether/maleic anhydride 1/1 copolymer M.W. 500,000 (GAF Corp.).
**Polyethylene glycol, M.W 600 (13–14 E.O.)
***Methyl ethyl ketone The PVM/MA copolymer is dissolved in the MEK (b.pt. 80° C.) yielding a 10 wt. % solution, in a stirred 1 liter resin kettle. The PEG is then added and the liquor refluxed for about 4 hours. At least 400 ml. of MEK are collected by distillation through a cold water condenser. A pink viscous syrup results which is poured at 50°–60° C. into a large evaporating dish and further devolatized under vacuum at 60°–70° C. overnight.

Though the starting PVM/MA copolymer is both ketone-soluble and water-soluble to a high degree, the products of both Examples 1 and 2 are pink, very hard solids, only slightly soluble in ketones, and insoluble but rapidly swelling in water to form gels. I.R. spectrum analyses show that the starting polymer has no free —COOH groups but both products show strong -COOH peaks resulting from ring opening and ester cross-links, indicative of an Example A product containing about 0.5 mole % or about 2 wt. % of PEG cross-linkages and an Example B product containing about 0.75 mole % or about 3 wt. % of PEG cross-linkages.

Concurrent Cross-Linking Polymerization

EXAMPLE C

In a one liter pressure reactor are charged the following: 404.4 parts cyclohexane, 269.6 parts ethyl acetate, and 6 parts 1,7 octadiene. 0.3 Parts of the initiator t-butylperoxypavilate are added at 58° C. in three increments of 0.1 part each at times: 0, 60, and 120 minutes from the first addition. Seventy-five parts of molten maleic anhydride and 49.0 parts of methyl vinyl ether are mixed together and gradually added to the reaction vessel at 58° C. and 65 psi (natural pressure of the system) over a 2 hour period of time. The reaction mixture is then held at 58° C. for two hours after the last addition of initiator. The presence of maleic anhydride is followed by testing with triphenyl phosphene. The product precipitates out of solution (slurry polymerization). After the reaction is complete, the product is cooled to room temperature, filtered and dried in a vacuum oven. It is a 1:1 cross-linked copolymer of methyl vinyl ether and maleic anhydride (PVM/MA) containing about 4.6 wt. % of the octadiene cross-linking agent.

EXAMPLE D

The procedure of Example C is repeated using 5 parts of 1,9-decadiene instead of the 6 parts of 1,7-octadiene. The product, in the form of a white powder, has the following viscosity specifications in varying concentrations in aqueous solution at pH 7 and 25° C. by Brookfield RVT, Spindle TC at 10 RPM:

TABLE 1

| Concentration | Viscosity |
|---|---|
| 0.25% | 30,800 cps |
| 0.50% | 63,500 cps |
| 1.00% | 90,000 cps |

An 0.5% aqueous solution of this product, Ph adjusted to 7 has the following viscosity properties when measured with a Brookfield Model RVT, Spindle TC, at varying RPM's:

TABLE 2

| RPM | Viscosity |
|---|---|
| 1 | $376 \times 10^3$ |
| 2.5 | $180 \times 10^3$ |
| 5 | $105 \times 10^3$ |
| 10 | $59 \times 10^3$ |

These results show that even at very low concentrations this cross-linked PVM/MA copolymer yields highly viscous solutions.

The following yield points of varying concentrations of this polymer in aqueous solution at pH 7 are obtained using the Haake Rotoviscometer RV12 with MV IP sensor system and shear rates varied from 0 to 10 sec$^{-1}$:

TABLE 3

| Concentration | Yield Point (Pascals) |
|---|---|
| 0.125 | 37 |
| 0.250 | 64 |
| 0.500 | 180 |

These high-yield points, corresponding to the amount of shear stress needed to initiate flow, indicate gel network formation enabling permanent stabilization of suspensions of particles such as insoluble polishing materials in dentifrice compositions.

EXAMPLE E

One percent aqueous solutions of cross-linked PVM/MA copolymer containing from 0.01% to 10% of 1,7-octadiene cross-linking agent, prepared as described in Example C, are shaken overnight in order to hydrolyze the maleic anhydride ring and then neutralized with NaOH to fully ionize the carboxyl groups. The results listed in the following table indicate that solutions containing more than 2.5%, i.e. at least about 3% of cross-linking agent gel whereas solutions containing up to 2.5% cross-linking agent do not gel.

TABLE 4

| Wt. % Cross-Linking Agent | Gelling Result |
| --- | --- |
| 0.1 | No gel |
| 0.5 | " |
| 1.0 | " |
| 2.5 | " |
| 5.0 | Gelled |
| 7.5 | " |
| 10.0 | " |

EXAMPLE F

Optional Hydrolysis Procedure

To a 2 liter kettle fitted with a mechanical agitator and a reflux column add 962 grams of deionized water and 28 grams of a 10% aqueous sodium hydroxide solution. Heat to 65° C. and add 10 grams of the product of Example D with stirring. The system becomes clear within 2 hours and has a pH of about 7. The resultant gel has a solids content of 1%.

The following examples are only illustrative of the dentifrice compositions of this invention. Typically, the cross-linked polymer or copolymer is hydrolyzed in water or water/humectant mixtures with a sufficient amount of base to neutralize the acid preferably at temperatures ranging from 40°–60° C. The resulting dispersion is mixed with the other dentifrice ingredients at a pH of about 7.

| | Opacified Dental Gel Formulations | | | |
| --- | --- | --- | --- | --- |
| | Weight Percent | | | |
| Example | 1 | 2 | 3 | 4 |
| XL Polymer A* | 0.5 | — | — | — |
| XL Polymer B** | — | 0.5 | 0.7 | — |
| XL Polymer C*** | — | — | — | 1.3 |
| Glycerine | 25.0 | — | 25.0 | 25.0 |
| Polyethylene Glycol 600 | 3.0 | — | 3.0 | 3.0 |
| Sorbitol (70% Aqueous Solution) | 31.7 | 62.8 | 34.8 | 35.2 |
| Sodium Hydroxide (50%) | 0.20 | 0.40 | 0.40 | 0.50 |
| NaF | 0.242 | 0.242 | 0.242 | 0.242 |
| Tetrasodium Pyrophosphate | 0.50 | 0.50 | 0.50 | 0.50 |
| Na Saccharin | 0.20 | 0.20 | 0.20 | 0.20 |
| TiO$_2$ | 0.30 | 0.30 | 0.30 | 0.30 |
| Na Benzoate | 0.50 | 0.50 | 0.50 | 0.50 |
| Zeodent 113 (SiO$_2$) | 18.0 | 23.0 | 23.0 | 23.0 |
| Sylodent 700 (SiO$_2$) | 5.5 | — | — | — |
| Flavor | 0.89 | 0.89 | 0.89 | 0.89 |
| Sodium Lauryl Sulfate (SLS) | 1.20 | 1.20 | 1.20 | 1.20 |
| Water, q.s. to | 100 | 100 | 100 | 100 |

| | Dental Cream Formulations | | |
| --- | --- | --- | --- |
| | Weight Percent | | |
| Example | 5 | 6 | 7 |
| XL Polymer B | 0.75 | 1.0 | 0.25 |
| Carboxymethyl Cellulose (CMC) | — | 1.3 | 0.5 |
| Glycerine | 19.9 | 10.2 | 25.0 |
| Polyethylene Glycol 600 | 3.0 | 3.0 | 3.0 |
| Sorbitol (70% Aqueous Solution) | 33.8 | 22.5 | 35.0 |
| NaOH (50%) | 0.3 | — | 0.3 |
| Tetrasodium Pyrophosphate | 0.5 | 1.5 | 0.5 |
| Tetrapotassium Pyrophosphate | — | 4.5 | — |
| Na Saccharin | 0.2 | 0.4 | 0.2 |
| TiO$_2$ | 0.3 | — | 0.3 |
| FD&C Blue #1 | — | 0.4 | — |
| Zeodent 113 (SiO$_2$) | 25.0 | 23.0 | 25.0 |
| Flavor | 0.89 | 0.95 | 0.89 |
| Sodium Lauryl Sulfate | 1.2 | 1.2 | 1.2 |
| Water, q.s. to | 100 | 100 | 100 |

| | Opacified Dental Gel Formulations | | |
| --- | --- | --- | --- |
| | Weight Percent | | |
| Example | 8 | 9 | Control A |
| Glycerine | 25.0 | 25.0 | 25.0 |
| Sorbitol (70% Aqueous Solution) | 36.2 | 36.2 | 38.1 |
| Polyethylene Glycol 600 | 3.0 | 3.0 | 3.0 |
| Carboxymethyl Cellulose (CMC) | 0.5 | — | 0.4 |
| Xanthan Gum | — | 0.4 | — |
| Xl Polymer B | 0.3 | 0.3 | — |
| Tetrasodium Pyrophosphate | 0.5 | 0.5 | 0.5 |
| Saccharin | 0.2 | 0.2 | 0.2 |
| NaF | 0.243 | 0.243 | 0.243 |
| TiO$_2$ | 0.3 | 0.3 | 0.5 |
| Flavor | 0.89 | 0.89 | 0.89 |
| Silica Thickener (Sylodent 15) | — | — | 5.5 |
| Silica Abrasive (Zeodent 113) | 20.0 | 20.0 | 18.0 |
| Sodium Lauryl Sulfate (SLS) | 1.2 | 1.2 | 1.2 |
| Water, q.s. to | 100 | 100 | 100 |

*Cross-linked PVM/MA of Example A containing about 0.5 mole % of PEG 600 cross-linking agent
**Cross-linked PVM/MA of Example C containing about 5 wt. % of 1,7-octadiene cross-linking agent
***Cross-linked PVM/MA of Example E containing about 10% of 1,7-octadiene cross-linking agent Viscosity Profiles Brookfield viscosities of the formulations of Examples 8, 9 and Control are measured as a function of time following the SPI No. 7707-1 procedure using Brookfield RVTD, spindle T-E, at 5 RPM, with the following results:

| | | | Brookfield Units | | |
| --- | --- | --- | --- | --- | --- |
| Formulation | % XL Polymer B | % Gum | 3 Days | 30 Days | 90 Days |
| Example 8 | 0.3 | 0.5 CMC | 23.5 | 25.0 | 28.5 |
| Example 9 | 0.3 | 0.4 Xanthan | 20.0 | 21.0 | 22.5 |
| Control A | — | 0.4 CMC | 29.0 | 38.0 | 41.5 |

The above results indicate substantially less progressive thickening with cross-linked polymer-containing formulations compared to a control containing CMC and silica thickener.

Stress Growth Test to Determine Dispensibility

Stress growth measurements to determine dispensibility of the dentifrice are performed using Rheometrics System Four instrument at constant shear rate of 10 sec$^{-1}$ and as function of time, with the following results.

| Formulation | Stress (Dynes/cm$^2$) |
|---|---|
| Example 8 | 7,500 |
| Example 9 | 6,000 |
| Control A | 9,500 |

The highest shear stress produced is indicative of the amount of work required to dispense the dentifrice. The above results indicate that cross-linked polymer-containing formulations are substantially easier to dispense than the control.

This invention has been described with respect to certain preferred embodiments and it will be understood that modifications and variations thereof obvious to those skilled in the art are to be included within the spirit and purview of this application and the scope of the appended claims.

We claim:

1. A linear viscoelastic dentifrice composition in the form of a toothpaste or dental gel with a pH of about 4 to about 9 comprising an orally acceptable water/humectant vehicle, an orally acceptable dental polishing agent and, in an amount effective to render the composition linearly viscoelastic, a synthetic linearly viscoelastic cross-linked polymeric thickening agent derived from a polymer containing repeating units in which one or more phosphonic acid groups are bonded to one or more carbon atoms in the polymer chain and having in a 1 wt. % aqueous solution an elastic or storage modulus G" and a viscous or loss modulus G" substantially independent of frequency in an applied frequency range of 0.1 to 100 radians/sec, a G' minimum value of 1,000 dynes/sq.cm which varies less than 1 order of magnitude of its original value, and a ratio of G"/G' ranging from more than 0.05 to less than 1.

2. A composition according to claim 1 containing approximately by weight, 6% to 50% of water, 20to 70% of humectant, 5 to 70% of dental polishing agent, and 0.02% to 5% of said polymeric thickening agent containing at least about 3% of cross-linking agent.

3. A composition according to claim 1 wherein the said polymeric thickening agent is made with a cross-linking agent containing at least two ethylenically unsaturated groups or at least two groups reactive with pendant reactive groups along the polymer chain of the polymeric thickening agent.

4. A composition according to claim 3 wherein said thickening agent is made with 1,7-octadiene, 1,9-decadiene, or polyethylene glycol as cross-linking agent.

5. A composition according to claim 4 wherein said polymeric thickening agent comprises units of styrene phosphonic acid, vinyl phosphonic acid and/or vinyl phosphonyl fluoride.

6. A composition according to claim 1 wherein the polymeric thickening agent has a molecular weight of about 1,000 to about 5,000,000 and comprises units of styrene phosphonic acid, vinyl phosphonic acid and/or vinyl phosphonyl fluoride.

7. A composition according to any one of claims 1, 2, 3, 4 or 5 wherein the polymeric thickening agent has a molecular weight of about 1,000 to about 5,000,000.

8. A composition according to any one of claims 1, 2, 3, 4 or 5 further containing an amount of a fluoride ion source sufficient to supply about 25 ppm to about 5,000 ppm of fluoride ions.

9. A composition according to claim 6 further containing an amount of a fluoride ion source sufficient to supply about 25 ppm to about 5,000 ppm of fluoride ions.

10. A composition according to claim 8 further containing about 0.4 to about 3 parts of xanthan gum or carboxymethyl cellulose per part of the cross-linked polymeric thickening agent.

11. A composition according to claim 9 further containing about 0.4 to about 3 parts of xanthan gum or carboxymethyl cellulose per part of the cross-linked polymeric thickening agent.

12. A method of promoting oral hygiene comprising applying to dental surface an effective amount of a composition as defined in any one of claims 1, 2, 4-6, 9 or 11.

13. A method of promoting oral hygiene comprising applying to dental surface an effective amount of a composition as defined in claim 8.

14. A method of promoting oral hygiene comprising applying to dental surface an effective amount of a composition as defined in claim 10.

* * * * *